(12) United States Patent
Govindaraj et al.

(10) Patent No.: US 10,644,889 B1
(45) Date of Patent: May 5, 2020

(54) CONSENT MANAGEMENT APPARATUS AND SYSTEM

(71) Applicant: Tetra Ventures LLC, New Brunswick, NJ (US)

(72) Inventors: Raghuraman Govindaraj, Princeton, NJ (US); Sharad Rao, Princeton, NJ (US); Sanjay Ungarala, New Brunswick, NJ (US)

(73) Assignee: TETRA VENTURES LLC, New Brunswick, NJ (US)

( * ) Notice: Subject to any disclaimer, the term of this patent is extended or adjusted under 35 U.S.C. 154(b) by 0 days.

(21) Appl. No.: 16/693,755

(22) Filed: Nov. 25, 2019

Related U.S. Application Data

(63) Continuation of application No. 16/687,653, filed on Nov. 18, 2019, now abandoned.
(Continued)

(51) Int. Cl.
| | |
|---|---|
| *H04L 9/32* | (2006.01) |
| *H04L 29/06* | (2006.01) |
| *G06F 9/54* | (2006.01) |
| *G06F 16/245* | (2019.01) |
| *G16H 40/20* | (2018.01) |
| *G06Q 50/26* | (2012.01) |
| *G06F 16/22* | (2019.01) |
| *G06K 7/14* | (2006.01) |
| *G06K 19/06* | (2006.01) |

(52) U.S. Cl.
CPC .............. *H04L 9/3247* (2013.01); *G06F 9/54* (2013.01); *G06F 16/22* (2019.01); *G06F 16/245* (2019.01); *G06Q 50/26* (2013.01); *G16H 40/20* (2018.01); *H04L 9/3236* (2013.01); *H04L 63/0853* (2013.01); *H04L 63/0861* (2013.01); *G06K 7/1417* (2013.01); *G06K 19/06037* (2013.01); *H04L 2209/38* (2013.01)

(58) Field of Classification Search
CPC . H04L 9/3247; H04L 9/3236; H04L 63/0853; H04L 63/0861; H04L 2209/38; G06F 16/22; G06F 9/54; G06F 16/245; G16H 40/20; G06Q 50/26; G06K 7/1417; G06K 19/06037
See application file for complete search history.

(56) References Cited

U.S. PATENT DOCUMENTS

| | | | |
|---|---|---|---|
| 9,602,282 B2 | 3/2017 | Hussain | |
| 9,608,829 B2 | 3/2017 | Spanos | |

(Continued)

*Primary Examiner* — Sonji N Johnson
(74) *Attorney, Agent, or Firm* — Ostrolenk Faber LLP

(57) ABSTRACT

A computer implemented apparatus and method is provided for authenticating a signature for a consent requiring permission of a person (i.e., a client) under supervision by a first agency for a service by a second agency, such as a service provider, wherein the service from the second agency is requested by the first agency. In the apparatus, the first agency requests a physical signature from the person. The request is made with a text message or QR code linking to a method (for example, a touch screen) for the person to create a signature. The signature and related account information such as the first agency, second agency, and identifying information on the person is entered into a distributed ledger database (DLTD) (e.g., a blockchain database) where it is archived. The service provider can query the DLTD for the signature for consent for the service.

17 Claims, 3 Drawing Sheets

Related U.S. Application Data

(60) Provisional application No. 62/880,487, filed on Jul. 30, 2019.

(56) References Cited

U.S. PATENT DOCUMENTS

| | | |
|---|---|---|
| 9,904,788 B2 | 2/2018 | Kumar |
| 10,148,641 B2 | 12/2018 | Iwanski |
| 10,163,080 B2 | 12/2018 | Chow |
| 10,361,849 B2 | 7/2019 | Smith |
| 10,380,366 B2 | 8/2019 | Bernau |
| 10,389,709 B2 | 8/2019 | Potlapally |
| 2018/0247385 A1* | 8/2018 | Whitfield ............. G06Q 50/265 |
| 2019/0348158 A1* | 11/2019 | Livesay .................. G06F 21/64 |

* cited by examiner

CONSENT MANAGEMENT APPARATUS AND SYSTEM

CROSS REFERENCE TO RELATED APPLICATION

This patent application is a continuation of U.S. patent application Ser. No. 16/687,653 filed Nov. 18, 2019, which claims priority to U.S. Patent Application 62/880,487 filed Jul. 30, 2019.

FIELD OF THE INVENTION

This invention pertains to a computer implemented apparatus for authenticating a signature for a consent requiring permission of a person under supervision by a first agency for a service by a second agency.

BACKGROUND

In situations with supervised environments, such as prisons, parole agencies, social welfare agencies, and schools, there is a demand for permission from clients for services, such as health care, mental health, and financial services, that can be difficult to manage. In such supervised environments, clients may not have the freedom to easily visit offices of service providers. Moreover, such clients may be expected to carry papers with them which presents a management problem, due to high rates of lost or misplaced papers, immaturity on the part of the client, uncooperative clients, and mental or physical impairments that prevent reliable exchanges of papers. At the same time, HIPAA and consent laws exist for the protection of clients and service providers so obtaining permissions and consents is a challenge. In many situations, ideally a consent would be arranged before a client actually visits a provider's office.

The ubiquity of smartphones and computer terminals can be used to address this problem. Thus, a smartphone, computer tablet, or other computing device can be used to request and capture essential information, including consent for a service that requires consent.

This invention also relies on distributed ledger technology databases for certain aspects to maintain secure record-keeping and avoid the need to clients and service providers to exchange paper documents.

Exemplary distributed ledger technologies include blockchain, Hedera Hashgraph and IOTA Tangle. A blockchain is a decentralized and distributed technology database (also termed a "ledger") used to record transactions. Copies of the ledger are stored across many computers so that the record cannot be altered retroactively without significant effort. A blockchain has specific rules about the data added to the blockchain database. That is, data added to the blockchain cannot conflict with other data that are already in the database (it must be consistent), can only append the blockchain (it must be immutable), the data are locked to an owner (ownable), and are replicable and available. Subjects (or members) in the blockchain must agree on the database rules (canonical).[1] A blockchain database is managed autonomously using a peer-to-peer network and a distributed timestamping server.

Hedera Hashgraph (HH)[2] is an alternative distributed ledger technology to blockchain. The technology uses an alternative distributed consensus to blockchain. This distributed consensus allows participants who don't know or trust each other to securely collaborate and transact online without the need for a trusted intermediary. HH has certain features in common with blockchain, but HH claims to have certain advantages of performance, security, governance, and stability as compared to blockchain technologies.

Another distributed ledger is an IOTA Tangle.[3] In an IOTA Tangle, transactions are not grouped into blocks and stored in sequential chains, but rather are stored as a stream of individual transactions "entangled" together. In order to participate in this network, a participant simply needs to perform a small amount of computational work that verifies two previous transactions. Rather than creating a hierarchy of roles and responsibilities in the network, every actor has the same incentives and rewards. In order to make a transaction in the Tangle, two previous transactions must be validated with the reward for doing so being the validation of your own transaction by some subsequent transaction. This is said to offer significant efficiencies as compared to blockchain technologies.[4]

Blockchain and other distributed ledger technologies are considered to be highly secure and resistant to tampering because each record (also termed a "block") contains a cryptographic hash of the prior block in the blockchain, linking the two records. Thus, a block cannot be changed without altering all subsequent blocks in the chain. Thus, each record in a distributed ledger database is essentially immutable, and therefore non-repudiable.

[1] For a good overview of the structure of blockchain databases, and the advantages and disadvantages of blockchain, see Jimmy Song, "Why Blockchain is Hard," published online May 14, 2018 at https://medium.com/jimmysonq/why-blockchain-is-hard-60416ea4c5c (visited Jun. 10, 2018)
[2] https://www.hederahashgraph.com/
[3] https://www.iota.org/
[4] https://www.iota.org/get-started/what-is-iota

SUMMARY OF THE INVENTION

In an embodiment, a computer implemented method is provided for authenticating a signature for a consent requiring permission of a person (i.e., a client) under supervision by a first agency for a service by a second agency, such as a service provider, wherein the service from the second agency is requested by the first agency.

In an embodiment, a computer implemented method and apparatus is provided for authenticating a signature for a consent requiring permission of a person under supervision by a first agency for a service required by the person from a second agency.

In an embodiment, the method or apparatus includes a computer implemented consent management service application programming interface (CMS API), a computer implemented consent requesting API (CR API), and a computer implemented consent authorizing application (CAA) is provided. In an embodiment, a person under the supervision of a first agency requires services from a second agency, and the services require consent from the person.

In an embodiment, the first agency issues an instruction to the CR API requesting the signature of the person within the context the services required. The CR API then issues an instruction to the CMS API, and the CMS API generates a signature context ID. The signature context ID is used to generate a QR code. The signature context ID is linked to identifying data on the person and the nature of the consent required.

In an embodiment, the QR code is communicated to the CR API, and the CR API displays the QR code on a computer screen or sends a message containing the signature context ID to a smartphone used by the person. The person (i.e., client), who has a smartphone or access to another computer device, receives instructions in the CAA running on the smart or other computer device, to scan the QR code or respond to the message. In an embodiment, an interface is then provided for the person to create a signature for consent. In an embodiment, the person then scans the QR code in the CAA with the smartphone or other computing device, or alternatively the person responds to the message. This establishes an interface to allow the CAA to capture a signature from the person signifying consent from the person to receive services from the second agency. Optionally, the CAA may capture the signature of the document along with a facial photograph of the person signing the document. In an embodiment, the signature and photograph is linked to the signature context ID.

In an embodiment, a computational representation of the signature and associated photograph is transmitted to the CMS API, and the CMS API creates a database record containing the signature context ID and the captured signature, such that the database record constitutes consent from the person to receive the services of the second agency. The database record is stored in a database such that each record in the database is immutable and each record in the database is securely linked to at least one previously created record in the database. In an embodiment, the second agency can query the database to receive the consent for the service provided by the second agency. In an embodiment, the second agency is assured that the consent is authentic because the database records are linked (for example with a cryptographic hash function), and because the records are immutable (non-repudiable). That is, once a record is created, it cannot be altered or deleted.

BRIEF DESCRIPTION OF THE DRAWINGS

FIG. 2 is a block diagram of a computing device according to an embodiment of this invention.

DETAILED DESCRIPTION

Figure 1:
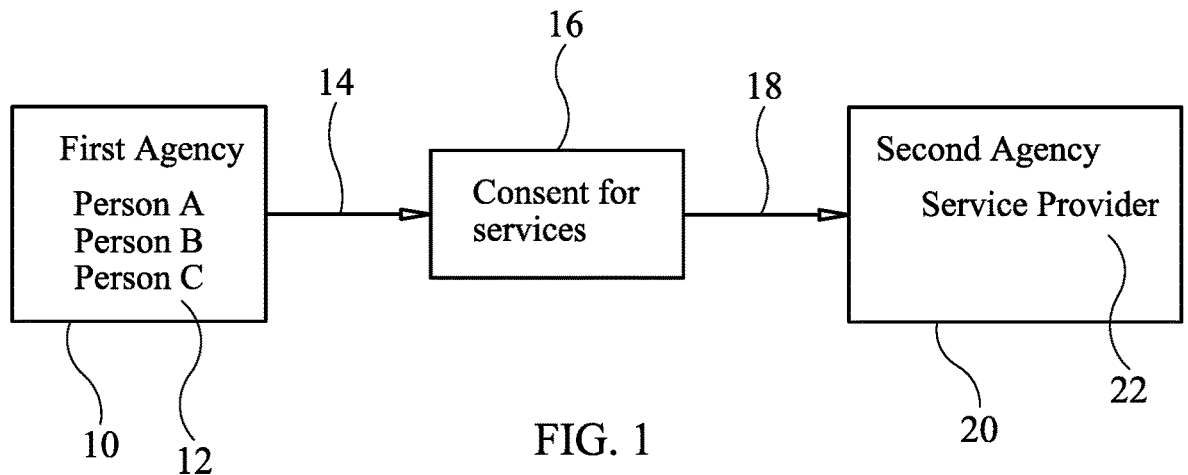
FIG. 1 is a block diagram showing high level overview of the invention, showing the overall flow of information.

In an embodiment, a computer implemented apparatus and method is provided for authenticating a signature for a consent 16 (FIG. 1) requiring permission of a person 12 (i.e., a client) under supervision by a first agency 10 for a service by a second agency 20 such as a service provider 22, wherein the service from the second agency is requested (14) by the first agency and the consent is provided (18) to the second agency. As used herein, "client" and "person," without another modifier in front of "person," are synonymous. A set of clients are depicted in FIG. 1 as persons A, B, and C (12).

Figure 2:
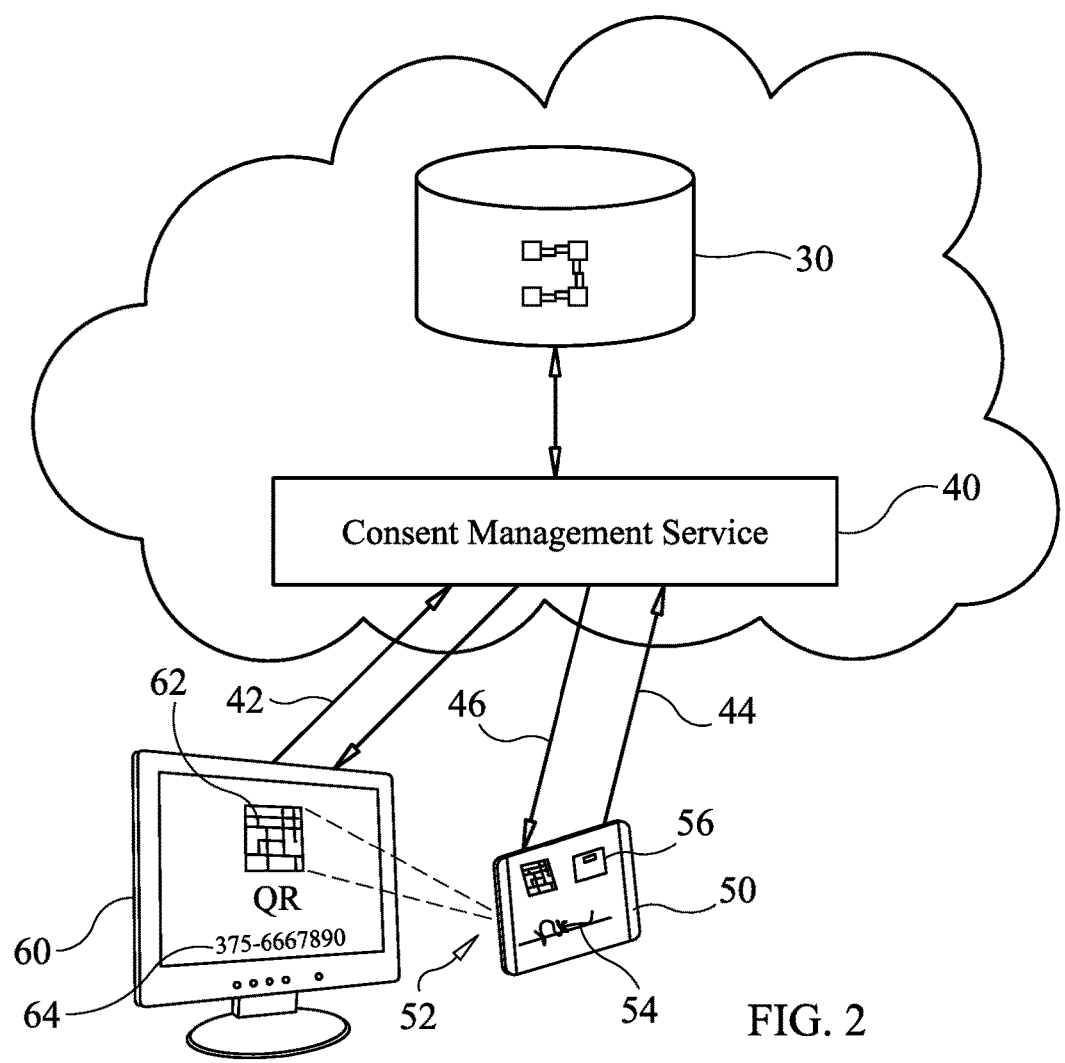
FIG. 2 is a schematic view of the architecture of the interaction of the consent management system, a database, and the capture of a signature for consent for services.

A high-level architectural overview of and embodiment of the invention is shown in FIG. 2. Consent management service 40 is linked to a database 30 that will store records of consents and other relevant information for use in the method. The consent management system enables an automated real time remote physical signature consent of the individuals participating or providing services to each other using authenticated devices. The need for the real time remote signing helps the providers to obtain consent from the clients and individuals willing to participate in the programs and provide legally mandated physical signature consent on a dynamic document created on the fly. The consent provided is recorded as an immutable (i.e., non-reputable) record in the database 30. As shown in FIG. 2, a data link 44 is provided to a smart phone or other computing device used by the client. At the same time, a data link 42 transmits a QR code 62 to a display device 60 such as a computer screen at the first agency. In an embodiment, a camera 52 on a smartphone 50 scans the QR code. Also depicted on display device 60 is an phone number 64 that can be used to authenticate the user instead of a QR code. This authenticates the user and the request, opening an interface for the capture of a signature 54 and optionally a photograph 56. The signature and optional photograph is transmitted (46) to the consent management system where it is processed into a database record representing consent for the service that can be queried by a second agency, i.e., a service provider who provides services requiring consent. The second agency is thus assured of the consent for services. Other variations not involving a QR code are within the scope of this invention. For example, a text message or system message may be sent to an authenticated device owned by the client that can serve the purpose of opening a signature capture interface In an embodiment, a computer implemented method and apparatus is provided for authenticating a signature for a consent requiring permission of a person under supervision by a first agency for a service required by the person from a second agency.

In an embodiment, the first agency may be a law enforcement agency selected from a prison, a parole agency, or a court-mandated agency. Examples of such agencies include anger management treatment facilities or drug abuse treatment facilities. Other first agencies are within the scope of this invention, including hospitals, other care facilities such as nursing homes or assisted living facilities, secure in-patient mental health facilities, and schools. This invention may be useful for any agency charged with the care and housing of people, in particular where the freedom of the people in the care of the first facility is limited for any of various legal or medical reasons. A particular advantage of this invention is that the consent can be obtained while the client is still physically located at a facility of the first agency (for example, a jail) to minimize delays and misunderstandings when a client is transported to a second agency or service provider or conditionally released and provides the consent remotely before receiving the service from the service provider. This invention may also be useful to a first agency may with supervisory responsibility over people that is not residential or in-patient.

The term "prison" here includes any lockup that incarcerates people, including facilities that may be termed a "jail", "detention center," "penitentiary," "correctional facility," etc. These facilities include may incarcerate people charged or convicted of crimes, while waiting trial, during trial, and serving sentences as punishment for crimes. The term "court mandated agency" here means any of various programs that a court orders people to participate in. These may include programs that restrict a person's freedom of movement. These include anger management programs, psychiatric treatment facilities, half-way houses, supervised residential facilities, out-patient or in-patient mental health facilities, and drug treatment programs.

Figure 3:
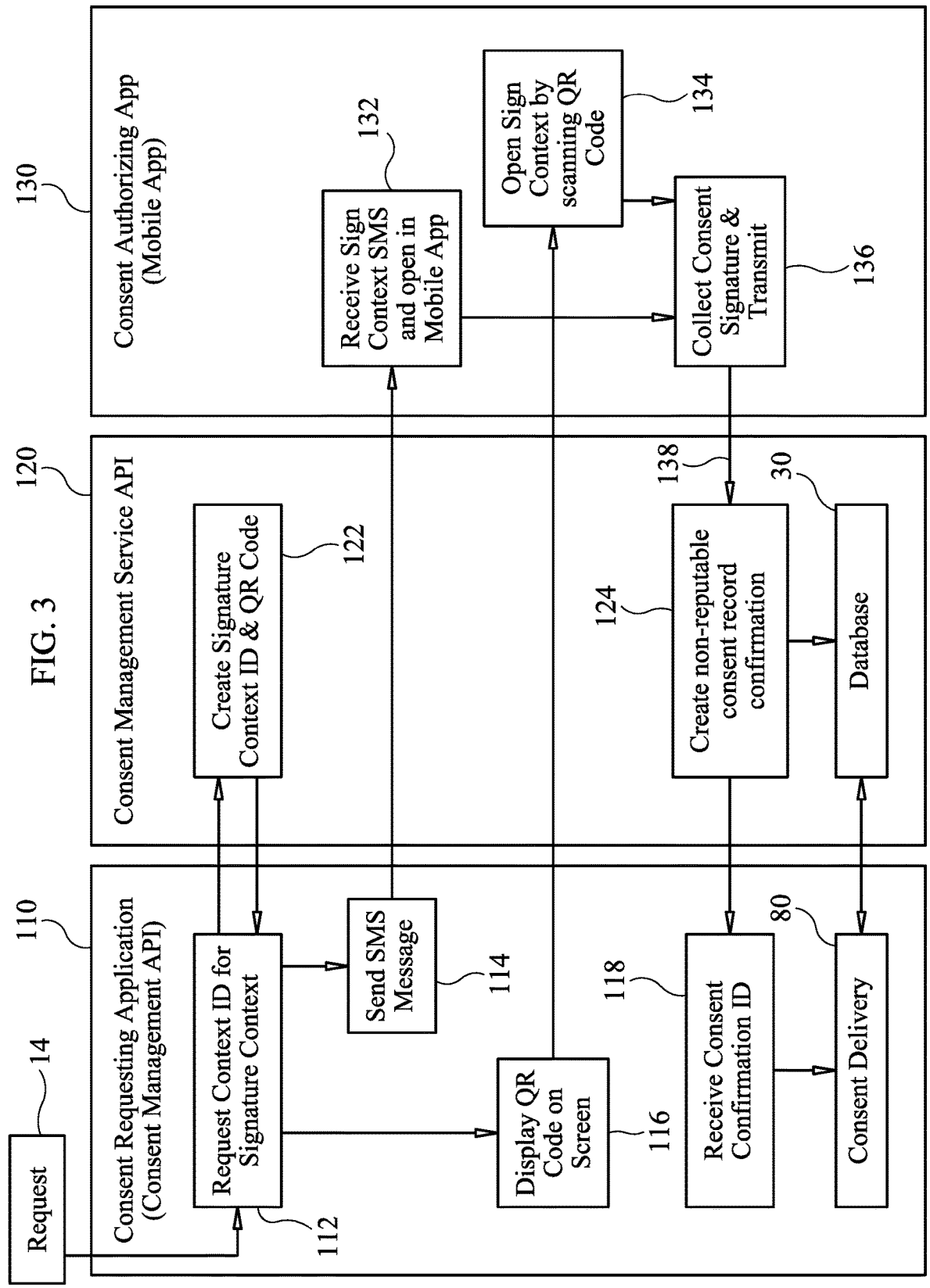
FIG. 3 is a block diagram of the various parts of the invention.

In an embodiment, the method or apparatus includes a computer implemented consent requesting API (CR API) 110 (FIG. 3), a computer implemented consent management service application programming interface (CMS API) 120, and a computer implemented consent authorizing application (CAA) 130. In an embodiment, the CAA may be a mobile application (app) running on a smartphone or a bar code scanner, or some other device that the client has access to or owns. In an embodiment the device running the CAA may be authenticated, meaning that all parties are assured that the particular device is owned by the client or that the client has authorized access to the device.

In an embodiment, a person under the supervision of a first agency requires services from a second agency, and the services require consent from the person. In an embodiment, the first agency issues an instruction to the CR API requesting the signature of the person within the context the services required (14, FIG. 3). The context means the nature of the services required, for example, mental health treatment or physical health treatment. The context may be specific to a specific provider or specific condition.

Some exemplary contexts may be services like ten psychotherapy sessions; an order for an imaging study (MRI, CT scan, or x-ray); a physician visit for an illness; or physician visit for treatment of a chronic condition such as hypertension. Another context may be one or more of informed consent for physical or mental health treatment, or Health insurance Portability and Accountability Act (HIPAA) consent (privacy and disclosure consents). In an embodiment, the context is limited to a specific set of services or treatment from a service providing agency and limited to a specific agency. For example, if the first agency seeks a service from a specific service provider, and the service is unable to provide that service, or there are delays or some other problem and a decision is made to seek an alternative service provider, a new signature would be required naming the alternative service provider.

In an embodiment, the CR API then issues an instruction to the CMS API, and the CMS API generates a signature context ID (122). The signature context ID may be used to generate a QR code (132). The signature context ID is linked to identifying data on the person and the nature of the consent required.

In an embodiment, a client may need services from more than one provider. For example, a particular individual may need medical treatment for a specific illness (for example, knee pain), and may also need psychotherapy. There will be different permissions and consents required for each service.

For any consent in this invention, there may be a time limitation component, i.e., that the consent is only valid for 30 days (for example). However, some services may be permanent, for example blood sugar monitoring in a diabetic. Other services may span a period of time such as six months.

In an embodiment, basic information on the client needs to be accounted for during the consent process, such as name, address, and other identifying information. In an embodiment, the signature context ID is linked to such information. In addition, other relevant information held by the first agency may be part of a record linked to a signature context ID, such as legal or medical history, or a criminal record. In an embodiment, some or all of this additional relevant information may be passed to the second agency as part of the consent process.

In an embodiment, the QR code is communicated to the CR API (112), and the CR API displays the QR code (116) on a computer screen or sends a text message (114) containing the signature context ID to a smartphone used by the person. The person (i.e., client), who has a smartphone or access to another computer device, receives instructions in the CAA running on the smartphone or another computer device accessible to the person, to scan the QR code (134) or respond to the text message (132). As illustrated in FIG. 2, the computer screen 60 may display a QR code (62 in FIG. 2) or a telephone number (64). Thus, in one embodiment, the person would scan the QR code with a smart phone camera 52, and the QR code would have an appropriate link or code to authenticate the person for the signature capture step. In an alternative embodiment, the person would send a text message, for example, via short message service (SMS) texting or rich content service (RCS) texting, to a telephone number 64 enabled for texting. The CR API and CAA would then work together to authenticate the person and open the signature capture component 136. Alternatively, the text message link can be transmitted to a person's smartphone as a system notification.

In an embodiment, an interface 136 is then provided for the person to capture a signature from the person signifying consent from the person to receive services from the second agency (20 in FIG. 1). In an embodiment, the signature may be captured with a touch screen, that a person can use to create a signature with the fingertip or a stylus adapted for writing on a computer screen. Such technology is well known in the art. In an embodiment, the signature is linked to the signature context ID. Other means of signifying consent may be employed in this invention. In some cases, a simple check box may suffice since the system can authenticate the user, so there is good assurance that the intended user is checking the box. Other means are possible too, such as a code from an authenticator application.

In an embodiment, interface 136 also captures a photograph of the person as the signature signifying consent is created. In an embodiment, interface 136 may employ any of several biometric identification and authentication methods. In an embodiment, facial recognition software to further assist in authentication and identification of the person giving consent. Exemplary facial recognition apps include "FaceFirst" and "SplitReef." In an embodiment, voice recognition software is employed to further assist in authentication and identification of the person giving consent. In this context, voice recognition software means software that identifies the person speaking, in contrast to software that converts speech to text. Exemplary software included Microsoft "Speaker Recognition," "NexalVoice" and "Knomi" from aware.com, and "VoiceKey" from Speechpro.com. In an embodiment, the biometric identification and authentication method may comprise fingerprint recognition. Typically, fingerprint recognition devices employ a special sensor, for example, a capacitive or ultrasonic sensor, and associated software to confirm the identification.

In an embodiment, a computational representation of the signature from interface 136, including a photograph and any biometric data if captured, is transmitted (138) to the CMS API, and the CMS API creates a database record (124) containing the signature context ID and the captured signature, such that the database record constitutes consent from the person to receive the services of the second agency. The database record is stored in a database 30 such that each record in the database is immutable and each record in the database is securely linked to at least one previously created record in the database.

In an embodiment, the second agency is notified of the consent (118) and can query the database 30 to receive the consent 80 for the service provided to be by the second agency. In an embodiment, the second agency is assured that the consent is authentic because the database records are linked (for example with a cryptographic hash function), and because the records are immutable (non-repudiable). That is, once a record is created, it cannot be altered or deleted.

In an embodiment, the permission from the client is not repudiable since each record is immutable, but permission can be revoked. That is, the client can revoke the consent and agreement to consent to services, but the client cannot repudiate that permission was granted at some time in the past. In an embodiment, this feature is enforced with immutable database records, which is an inherent feature of a distributed ledger technology database (DLTD). DLTD records (also termed "blocks") are immutable. Accordingly, in an embodiment, a revocation would involve the creation of a new database record.

In an embodiment, the first agency or the client issues an instruction to the CR API requesting the signature of the person within the context the services required. In alternative embodiments, the client may initiate the request themselves, rather than relying on the first agency to initiate the request.

In an embodiment, the text message may be an SMS text or a text message sent on some other computer application, for example, WhatsApp, Facebook Messenger, Viber, Snapchat, and others. The message may be transmitted as a system message, that appears as a pop-up from the smartphone operating system. In an embodiment, a custom app may be provided for users of this system that includes enhanced security, confidentiality, and functional features not available on commonly used messaging apps. In particular, a custom app may be specifically linked to the CAA of this invention.

In an embodiment, the message sent to a smartphone that includes the unique identifier or a second identifier is linked to the signature context ID. In an embodiment, the message is a text message or a system notification message on the smartphone. A QR code serves the same function of linking a unique identifier to a signature context ID.

In an embodiment, the actual consent is provided by a signature from the client. In an embodiment, this may be accomplished by the person scanning the QR code with the smartphone or by opening the text message and clicking or otherwise activating a link, and wherein the QR code and identifier codes in the text message are linked to a computer interface controlled by the CAA. In an embodiment, the computer interface captures a signature from the person signifying consent from the person to receive services from the second agency, such that the signature is linked to the unique identifier. In an embodiment, the signature capture may include a photograph of the person.

In an embodiment, the computer interface controlled by the CAA is an application running on the smartphone of the person, or is a computer tablet, laptop, or desktop computer owned and operated by someone else. Exemplary smartphones include iPHONE® phones or ANDROID™ phones. Various tablets based on varying computer operation systems may be use in computer tablets, laptops, or desktops. For example, for a person who does not own a smartphone, a tablet, laptop, or desktop in an office may be the best approach to using this invention.

In an embodiment, a computational representation of the signature comprises a graphical representation of a hand-drawn signature, and optionally a photograph of the person as the signature is captured, or optionally a another biometric identifier selected from a fingerprint, facial recognition, or corneal scan, or another data entry providing assurance that the person consents to the services provided by the second agency. In an embodiment, the computational representation of the signature is subjected to a cryptographic hash function and assigned a unique hash value that is stored in the database.

There are several ways signatures for the consent of this invention can be collected from a client. In an embodiment, the signature may be an electronic signature (e-signature or digital signature), which has many potential forms. An e-signature should provide the same legal standing as a handwritten signature provided it adheres to the requirements of the specific regulation it was created under. For example, the United States Food and Drug Administration (FDA), which creates standards for healthcare-related services, defines an electronic signature as "a computer data compilation of any symbol or series of symbols executed, adopted, or authorized by an individual to be the legally binding equivalent of the individual's handwritten signature." (21 CFR 11.3). The FDA also defines a digital signature as "an electronic signature based upon cryptographic methods of originator authentication, computed by using a set of rules and a set of parameters such that the identity of the signer and the integrity of the data can be verified." Other forms of consent may be employed in this invention, for example a biometric identifier, such as a fingerprint captured with a fingerprint reader, a retinal or iris eye scan, or facial recognition captured with facial recognition software. In another embodiment, a person may sign with a special pen on a computer screen.

Regardless of the method of capture, the signature must be reduced to a data format that can be readily stored in the distributed ledger database. This may be a graphic data file, for example a jpg or tiff file, or an alphanumeric data representation. The electronic signature, regardless of the format, may be subjected to a cryptographic hash function to receive a unique hash value (also termed a "digest") for use in authenticating the signature. The hash value may be incorporated into the database record representing consent.

In an embodiment, the second agency can query the DLTD to receive consent for the service provided by the second agency, and wherein the second agency is assured that the consent is authentic. The consent has assured authenticity from the nature of this entire apparatus and procedure that provides a fully traceable provenance of the consent.

Thus, the inventive apparatus and method avoids the need for clients to fill out forms on paper and potentially carry papers from one place to another. The entire consent and context process is handled electronically, from ordering the services, to granting of consent, and finally conveyance of the consent to a service provider that require consent for a particular service for the client.

Even though the term "second agency" is used to denote a service provider, a service provider may not be an "agency" in the conventional definition of the term. A second agency within the scope of this invention may be a physician's office or psychotherapist not employed by a larger organization.

In an embodiment, the method includes providing consent for personal information to be transmitted from the first agency to the second agency. In an embodiment, the first agency likely has relevant information on the person (client), such as medical history, relevant legal history, or other documentation relevant to the consent for a service sought by the person from the second agency. Thus, by permitting the consent to also include transmission of information from the first agency to the second agency can insure more accurate transmission of data that can streamline the entire process.

The inventive method requires a database system. In an embodiment, the database is a distributed ledger technology database (DLTD) such as a blockchain database, Hedera Hashgraph, or IOTA. In an alternative embodiment, the database is a non-relational database, which is often termed a "NoSQL". Examples include MarkLogic, MongoDB, Datastax, Apache Cassandra, Redis, Riak, Google BigTable and CouchDB.

DLTD implementations have three key features: (1) decentralization; (2) cryptographically linked records (blocks); and (3) immutability. In a decentralized system, data is stored across a plurality of devices that are kept synchronized continually. Each record (also called a "block") is linked to at least one previously created block in the database (i.e., the "chain") with a cryptographic hash function. In turn, at least one block created later in time will link to any block with a cryptographic hash. This feature is critical for the immutability aspect of DLTD's. Because all the blocks are linked with hash functions, it is impossible to alter or remove a record once it is created. That would destroy the integrity of the database. Thus, DLTD's are inherently highly secure. A database record, once created, cannot be deleted or altered, and the database is stored across a network so an attack or equipment failure at any particular device should not affect other nodes on the network. These are all important features in the instant invention.

An alternative database embodiment can employ another underlying technology that provides the security and immutable features of a DLTD with alternative mechanisms. In an embodiment, the alternative database can be a "NoSQL"—type of database. In an embodiment, a NoSQL database must have ACID properties (atomicity, consistency, isolation, and durability). Many ACID features may be inherent in a DLTD but may need to be explicitly implemented in a NoSQL database. Popular NoSQL implementations that may be useful in this invention include Apache Cassandra and MongoDB.

Figure 4:
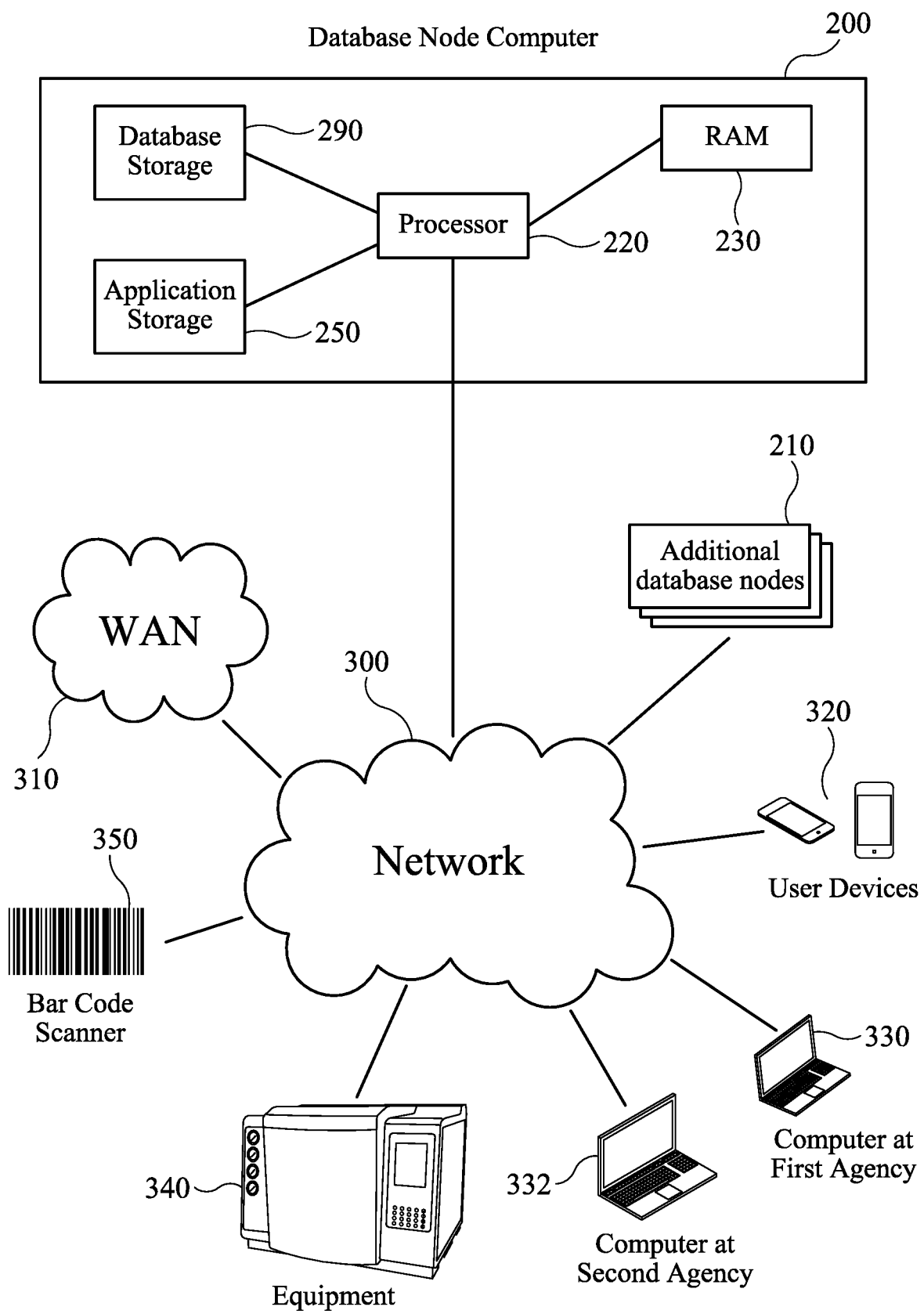
FIG. 4 is a schematic view of an apparatus according to this invention, showing the interaction of a computer network with a database computer node and various devices linked to the network.

FIG. 4 schematically illustrates an exemplary computing environment in which a DLTD platform can be implemented. FIG. 4 provides a plurality of database node computers 200 and 210, each of which is a peer participant in the DLTD. Each computer includes typical computer hardware, such as a processor 220, random access memory 230, data storage 240, and application storage 250. The computer 200 is connected to a network 300. Network 200 in turn supports a plurality of additional devices. For example, additional database node computers 210 may be connected. User devices 320 may be connected, (i.e., devices used by clients in this invention) such as smart phones or personal computers. Computer terminals may be connected, such as computers at a first agency 330 or a second agency 332. The computer terminals 330 and 332 may be tabletop computers, laptops, mobile computers, or handheld devices including smartphones. Equipment 340 that captures data may be connected, for example gas chromatographs, liquid chromatographs, mass spectrometers, scales, photographic equipment, blood alcohol measuring equipment, blood pressure measuring devices, blood sugar measuring devices, or other technical or medical measuring equipment that generates data that may be required for the consent signatures in this invention or for related information. Barcode scanners 350 may be connected, to scan QR codes. Other input devices are possible also. The network may be connected to a wide-area network 310, such as the public internet. This allows far-flung equipment to communicate with each other.

In an embodiment, a distributed ledger technology database may be a blockchain, a Hashgraph, or an IOTA database. As used herein, a distributed ledger technology refers to a distributed storage platform and network in which individual "blocks" of data are connected in a chain or network. Hashgraph and IOTA have non-linear architectures and are arrangements in which non-linear networks of blocks are woven together. Each block in the non-linear architecture embodiments is connected to at least two other blocks. The network is not constructed in a linear fashion, as in blockchain. Both Hashgraph and IOTA claim to have performance enhancements compared to the linear blockchain architecture. As with blockchain, the connections in Hashgraph and IOTA rely on encryption and hash functions in the links between blocks.

Each block in a blockchain DLTD may be linked to the previous block in the blockchain by, for example, including a hash of the previous block as a "proof of work." Various hash functions, including functions in the Secure Hash Algorithm (SHA)-1 or -2 families, such as SHA-256, can be used to perform a one-way hash. For a one-way hash, it is generally considered to be impossible or impractical to generate the input (the "message") to the hash function based on the output (the "message digest" or "digest") of the hash function. Thus, it is extremely difficult (if not impossible) to alter records or the chain by disturbing the links between blocks. The database integrity requires that each block includes a hash digest from at least one other block. In turn, the hash digest of the contents of each block are referred to by at least one other block created later in time. Moreover, if the database is truly distributed across multiple instances and kept synchronized, then it becomes impossible to corrupt any particular instance (for example, by creating a bad block without a proper hash digest or altering a block) without the problem being detected across the network. If this happens, the synchronization is prevented by system rules, thus preserving the integrity of the DLTD.

In a blockchain or other DLTD, each database block can store a variety of data that may or may not be related. That is, the contents of any pair of adjacent records may or may not be associated with a same user or may or may not have the same type of data. For example, one block may have analytical data such as a mass spectrum, and an adjacent block may have a signature and a consent form. However, each block in the DLTD is linked to adjacent blocks with cryptographic metadata that links to other blocks, and that other blocks can link to. That is, the linking data is two-way. A feature of any DLTD is that the entire database is replicated on multiple devices such as computing devices 200 or on additional nodes 210 in FIG. 4. In an embodiment, the nodes are peers, on a peer-to-peer network. By the term "node," it is meant a computer such as device 200 that stores the entire distributed ledger. In a DLTD according to this invention, the database is updated continuously in real time across multiple nodes. As new records are added, they are linked to preexisting records via their metadata and hash functions. Peer-to-peer (P2P) computing or networking is a distributed application architecture that partitions tasks or workloads between peers. Peers are equally privileged, equipotent participants in the application. Thus, with a P2P DLTD, there is no "master copy"—each node has a complete copy of the DLTD that is updated continuously in real time as new data (i.e., blocks)

The metadata in each database record includes data linking that record to other records, for example a hash value, and that other records link to in turn. In various embodiments, the metadata may also include data such as a timestamp that the record was created, the name of the user or the device that created the data, the type of data (for example, analytical data, audit results, audit completion, patient records, clinical results, or batch records). Much of this data may need to be standardized or normalized. For example, each user may have a username so that the usage is consistent. Similarly, each piece of equipment may also need to have a standard ID or computer name, so a person reviewing the records can immediately recognize the source of the data.

The metadata and security features outlined herein, that are largely inherent in any DLTD implementation, create relationships of trust between participants in the DLTD (trusted relationships). The records are safe and reliable, and any authorized participant (human, or automated devices) can create a record, and any authorized person can read or edit a record. This gives participants peace of mind that the data has integrity.

DRAWINGS LEGEND

| | |
|---|---|
| 10 | First agency |
| 12 | Persons (clients) affiliated with first agency |
| 14 | Request for services |
| 16 | Consent for services |
| 18 | Delivery of consent to second agency |
| 20 | Second agency service provider |
| 22 | Service provider |
| 30 | Database |
| 40 | Consent Management Service (CMS) |
| 42 | Data link to CMS for display of QR code |
| 44 | Data link from CMS to smartphone for beginning transaction |
| 46 | Data link from smartphone to CMS with confirmation of code and signature |
| 50 | Smartphone |
| 52 | Camera on smartphone |
| 54 | Signature captured on smartphone |
| 56 | Photograph of person signing captured on smartphone |
| 60 | Computer terminal showing QR code |
| 62 | QR code |
| 64 | Text phone no. alternative to QR code |
| 80 | Consent delivery to service provider |
| 100 | Consent management apparatus |
| 110 | Consent requesting application (CR API) |
| 112 | Request context ID for consent |
| 114 | Send message to smartphone |
| 116 | Display of QR code on computer terminal |
| 118 | Receive consent confirmation |
| 120 | Consent management service API (CMS API) |
| 122 | Creation of signature context ID and QR code |
| 124 | Create database record |
| 130 | Consent authorizing app (CAA) on mobile device |
| 132 | Receive context instruction by message |
| 134 | Scan QR code on smartphone |
| 136 | Capture signature |
| 138 | Transmit signature to CMS API |
| 200 | Database node computer |
| 210 | Additional database nodes |
| 220 | Processor |
| 230 | Random Access memory |
| 240 | Data storage |
| 250 | Application storage |
| 300 | Network |
| 310 | Wide area network |
| 320 | User devices, such as smartphones |
| 330 | Computer terminal at first agency |
| 332 | Computer terminal at second agency (service provider) |
| 340 | Other equipment |
| 350 | Barcode/QR code scanners |

The invention claimed is:

1. A computer implemented method for authenticating a signature for a consent requiring permission of a person under supervision by a first agency for a service from a second agency required by the person, comprising
   a. Providing a computer implemented consent management service application programming interface (CMS API), a computer implemented consent requesting API (CR API), and a computer implemented consent authorizing application (CAA);
   b. wherein a person under the supervision of a first agency requires services from a second agency, and wherein the services require consent from the person;
   c. wherein the first agency issues an instruction to the CR API requesting the signature of the person within the context the services required;
   d. wherein the CR API issues an instruction to the CMS API, and wherein the CMS API generates a signature context ID, and wherein the signature context ID is used to generate a QR code, wherein the signature context ID is linked to identifying data on the person and the nature of the consent required;
   e. wherein the QR code is communicated to the CR API, and the CR API displays the QR code on a computer screen or sends a text message containing the signature context ID to a smartphone or other device used by the person;
   f. wherein the person receives instructions in the CAA which is installed and running on a smartphone or other computing device to scan the QR code or respond to the message, and an interface is then provided for the person to create a signature for consent;
   g. wherein the person scans the QR code in the CAA with the smartphone or other computing device, or wherein the person responds to the text message, and wherein the CAA opens a signature interface that captures a signature from the person signifying consent from the person to receive services from the second agency, such that the signature is linked to the signature context ID;
   h. wherein a computational representation of the signature is transmitted to the CMS API, and the CMS API creates a database record containing the signature context ID and the captured signature, such that the database record constitutes consent from the person to receive the services of the second agency, and the database record is stored in a database such that each record in the database is immutable and each record in the database is securely linked to at least one previously created record in the database; and
   i. wherein the second agency queries the database to receive the consent for the service provided by the second agency, and wherein the second agency is assured that the consent is authentic.

2. The method of claim 1, wherein the first agency is a law enforcement agency selected from a prison, a parole agency, or a court-mandated agency.

3. The method of claim 1, wherein the first agency is selected from a hospital, a medical care facility, or a school.

4. The method of claim 1, wherein a photograph of the person is taken at the same time the signature representing consent is captured.

5. The method of claim 1, wherein a biometric authentication method is used at the same time the signature representing consent is captured, wherein the biometric authentication method is selected from facial recognition, voice recognition, and a fingerprint, or a combination thereof.

6. The method of claim 1, wherein the nature of the consent required for the service provided by the second agency is selected from a mental health service or a physical healthcare service.

7. The method of claim 1, wherein the nature of the consent includes consent for providing personal information pertaining to the person held by the first agency to the second agency.

8. The method of claim 1, wherein the consent required includes one or more of informed consent for physical or mental health treatment, and HIPAA consent.

9. The method of claim 1, wherein the database enforces immutable records.

10. The method of claim 1, wherein the database is a distributed ledger technology database (DLTD).

11. The method of claim 10, wherein the DLTD is a blockchain.

12. The method of claim 1, wherein the secure link of each record in the database to at least one other previously created record relies on a cryptographic hash function.

13. The method of claim 1, wherein the computational representation of the signature is subjected to a cryptographic hash function and assigned a unique hash value.

14. The method of claim 1, wherein the CAA is an application running on the smartphone of the person, or is a computer tablet, laptop, or desktop computer owned and operated by someone else for the purpose of capturing a signature for consent.

15. The method of claim 1, wherein the computational representation of the signature comprises a graphical representation of a hand-drawn signature, a biometric identifier selected from a fingerprint, facial recognition, or corneal scan, or another data entry providing assurance that the person consents to the services provided by the second agency.

16. The method of claim 1, wherein the text message sent to a smartphone that includes the unique identifier or a second identifier that is linked to the signature context ID is a text message or a system notification message on the smartphone.

17. An apparatus for capturing and recording a signature required for consent for a person under supervision by a first agency for a service required by the person from a second agency, comprising a. a computer implemented consent management service application programming interface (CMS API), a computer implemented consent requesting API (CR API), and a computer implemented consent authorizing application (CAA) is provided;
   b. wherein a person under the supervision of a first agency requires services from a second agency, and wherein the services require consent from the person;
   c. wherein the first agency issues an instruction to the CR API requesting the signature of the person within the context the services required;
   d. wherein the CR API issues an instruction to the CMS API, and wherein the CMS API generates a signature context ID, and wherein the signature context ID is used to generate a QR code, wherein the signature context ID is linked to identifying data on the person and the nature of the consent required;
   e. wherein the QR code is communicated to the CR API, and the CR API displays the QR code on a computer screen or sends a message containing the signature context ID to a smartphone used by the person;
   f. wherein the person receives instructions in the CAA which is installed and running on a smartphone or other computing device to scan the QR code or respond to the message, and an interface is then provided for the person to create a signature for consent;
   g. wherein the person scans the QR code in the CAA with the smartphone or other computing device, or wherein the person responds to the message, and wherein the CAA captures a signature from the person signifying consent from the person to receive services from the second agency, such that the signature is linked to the signature context ID;
   h. wherein a computational representation of the signature is transmitted to the CMS API, and the CMS API creates a database record containing the signature context ID and the captured signature, such that the database record constitutes consent from the person to receive the services of the second agency, and the database record is stored in a database such that each record in the database is immutable and each record in the database is securely linked to at least one previously created record in the database; and
   i. wherein the second agency can query queries the database to receive the consent for the service provided by the second agency, and wherein the second agency is assured that the consent is authentic.

* * * * *